United States Patent
Yasuda et al.

(10) Patent No.: US 6,706,885 B2
(45) Date of Patent: Mar. 16, 2004

(54) PROCESS FOR PREPARING INTEGRIN ANTAGONIST INTERMEDIATES

(75) Inventors: Nobuyoshi Yasuda, Mountainside, NJ (US); Michael Palucki, Hillsborough, NJ (US); Yi Xiao, Fanwood, NJ (US); Frederick W. Hartner, Somerville, NJ (US); Lushi Tan, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/191,042

(22) Filed: Jun. 5, 2002

(65) Prior Publication Data

US 2003/0004353 A1 Jan. 2, 2003

Related U.S. Application Data

(60) Provisional application No. 60/296,253, filed on Jun. 6, 2001.

(51) Int. Cl.$^7$ ............................................. C07D 213/53
(52) U.S. Cl. ...................... 546/329; 546/334; 546/335
(58) Field of Search ................................ 546/329, 334, 546/335

(56) References Cited

FOREIGN PATENT DOCUMENTS

| | | |
|---|---|---|
| GB | 2356630 | 5/2001 |
| WO | WO 01/34602 | 5/2001 |

OTHER PUBLICATIONS

Cram and Hammond, "Organic Chemistry" McGraw Hill Book Co., NY (1964) 2nd Ed., pp 565–67.*
H. Yinglin, et al., Synthesis, (1990), pp. 122–124, "A Convenient Synthesis of Primary Amines Using Sodium Diformylamide as A Modified Gabriel Reagent".
J. Dumont, et al., Bull. Soc. Chem. Fr., No. 2, (1967), pp. 588–596, "Contribution a l'etude des amines w–acetyleniques vrais et de leurs derives".

* cited by examiner

Primary Examiner—Patricia L. Morris
(74) Attorney, Agent, or Firm—Patricia A. Shatynski; Mark R. Daniel

(57) ABSTRACT

A novel process is provided for the preparation of optionally protected 2,5-di-(3'-aminopropyl)-pyridines which are useful in the synthesis of αv integrin receptor antagonists. Also provided are useful intermediates obtained from the process.

17 Claims, No Drawings

PROCESS FOR PREPARING INTEGRIN ANTAGONIST INTERMEDIATES

CROSS-REFERENCE TO RELATED APPLICATIONS

The present invention is related to U.S. provisional application Serial No. 60/296,253, filed Jun. 6, 2001, the contents of which are hereby incorporated by reference.

FIELD OF THE INVENTION

The present invention discloses a novel process and novel intermediates toward the preparation of optionally protected 2,5-di-(3'-aminopropyl)pyridines which are useful in the synthesis of αv integrin receptor antagonists.

BACKGROUND OF THE INVENTION

The present invention provides a novel process for the preparation of optionally amino group-protected 2,5-di-(3'-aminopropyl)pyridines of structural formula I,

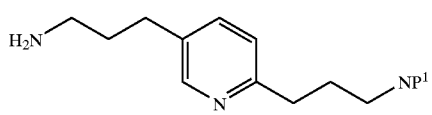
(I)

wherein $P^1$ is $H_2$ or a primary amine protecting group. The present invention also provides novel intermediates useful in the disclosed process.

The synthesis of the compound of formula I wherein $P^1$ is $H_2$ was previously disclosed in UK Patent Application GB 2,356,630 (May 30, 2001). In that publication, the 2,5-bis-substituted pyridine ring system was constructed by means of a one-pot double Suzuki cross-coupling of a 2,5-dihalopyridine with a protected allylamine in the presence of 9-BBN and subsequent removal of the primary amine protecting groups.

In the present invention, the compound of formula I wherein $P^1$ is $H_2$ is produced in a highly efficient manner in a total of three chemical steps featuring a one-pot double Sonogashira reaction of a 2,5-dihalopyridine with an optionally protected propargylamine, followed by hydrogenation, and final cleavage of the primary amine protecting groups $P^1$, if required.

The compounds of formula I wherein $P^1$ is a primary amine protecting group are also prepared in an efficient fashion by two consecutive Sonogashira reactions with orthogonally protected propargylamines, followed by hydrogenation, and removal of protecting group $P^2$ on the aminopropyl functionality at the C-5 position of the pyridine ring leaving the aminopropyl group at the C-2 position of the pyridine ring protected with $P^1$.

SUMMARY OF THE INVENTION

This invention is concerned with a process for preparing optionally amino group-protected 2,5-di-(3'-aminopropyl)pyridines of structural formula I, wherein $P^1$ is $H_2$ or a primary amine protecting group, and useful intermediates obtained during that process. The process utilizes a double Sonogashira reaction of a 2,5-dihalopyridine with optionally protected propargylamines, hydrogenation, and final removal of the primary amine protecting group, if required.

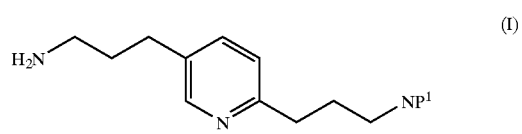
(I)

The novel process and novel intermediates are illustrated in the following embodiments denoted in Schemes 1 and 2 below. Scheme 1 illustrates the preparation of the compound of formula I wherein $P^1$ is $H_2$.

SCHEME 1

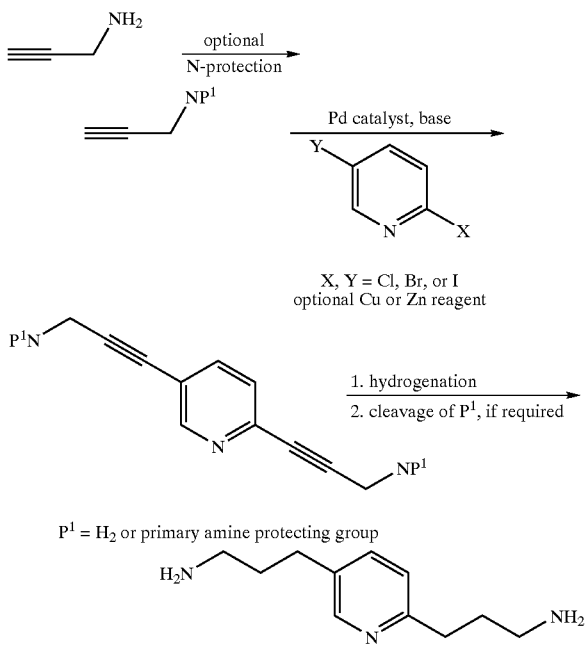

Scheme 2 illustrates the preparation of compounds of formula I wherein $P^1$ is a primary amine protecting group.

SCHEME 2

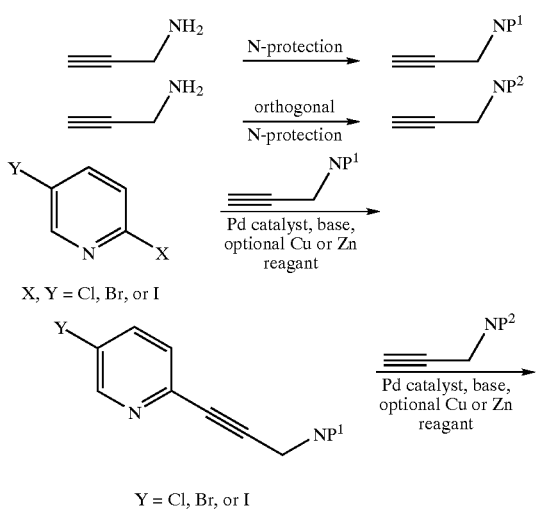

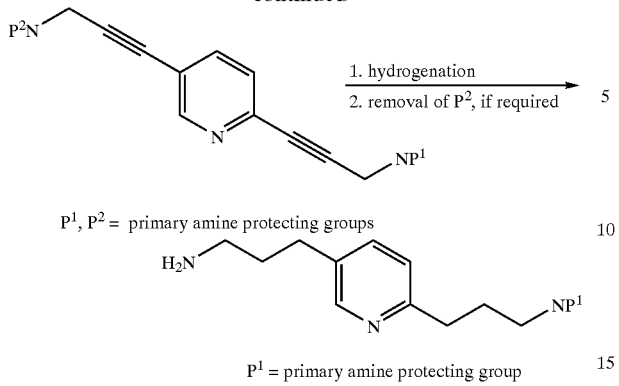

P¹, P² = primary amine protecting groups

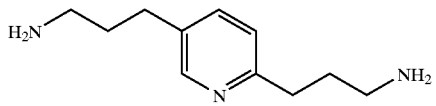

P¹ = primary amine protecting group

Another aspect of the present invention is concerned with an improved process for the preparation of N-formylpropargylamine, a substrate for the Sonogashira reaction disclosed herein.

DETAILED DESCRIPTION OF THE INVENTION

One aspect of the process of the present invention involves the preparation of the compound of structural formula Ia:

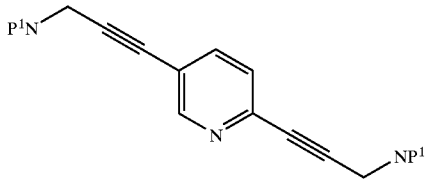

comprising the steps of:

(a) producing a compound of structural formula II:

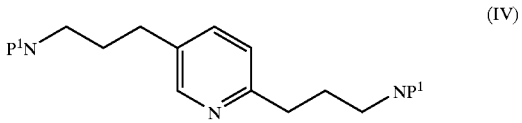

wherein P¹ is H₂ or a primary amine protecting group, by reacting a 2,5-dihalopyridine with an optionally protected propargylamine of structural formula III:

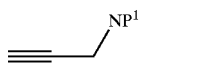

in the presence of a palladium catalyst and a base;

(b) producing a compound of structural formula IV:

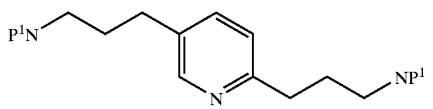

by hydrogenating a compound of structural formula II:

(II)

$P^1N$ ... $NP^1$ and (c) removing the primary amine protecting groups P¹ in a compound of structural formula IV:

(IV)

$P^1N$ ... $NP^1$ when P¹ represents a primary amine protecting group.

The key steps in this first aspect of the process of the present invention include a double Sonogashira reaction of a 2,5-dihalopyridine with an optionally protected propargylamine, hydrogenation, and removal of the primary amine protecting groups, if necessary.

One substrate for the double Sonogashira reaction is an optionally protected propargylamine. In one embodiment of the process of the present invention, the propargylamine is protected as its N-acetyl derivative. This is accomplished by treatment of propargylamine with acetic anhydride or acetyl chloride in a suitable solvent, such as methylene chloride, tetrahydrofuran, toluene, hexane, ethyl acetate, isopropyl acetate, water, lower alkanol, and aqueous lower alkanol, or mixtures thereof.

In a second embodiment of the process of the present invention, the propargylamine is protected as its N-formyl derivative. This is accomplished by treatment of a propargyl halide, a propargyl $C_{1-4}$ alkylsulfonate, such as propargyl methanesulfonate, propargyl trifluoromethanesulfonate, a propargyl arylsulfonate, such as propargyl benzenesulfonate and propargyl p-toluenesulfonate, or a propargyl di($C_{1-4}$ alkyl)phosphate with an alkali metal diformylamide, such as sodium diformylamide, in a suitable organic reaction solvent, such as acetonitrile, tetrahydrofuran, DMF, and the like. One of the two formyl protecting groups in the resulting N,N-diformylpropargylamine is then cleaved by treatment with an inorganic base, such as potassium carbonate, sodium carbonate, potassium hydroxide and sodium hydroxide, in the presence of methanol or ethanol, preferably one to two molar equivalents thereof, to afford N-formylpropargylamine, the substrate for the Sonogashira reaction of the present invention. In one embodiment, An alternative but less economical synthesis of N-formylpropargylamine was described in *Bull. Soc. Chim. Fr.*, 588 (1967). The use of sodium diformylamide as a modified Gabriel reagent for the synthesis of primary amines was described in *Synthesis*, 122–124 (1990).

Other amine protecting groups may also be used and include t-butyloxycarbonyl (Boc), benzyloxycarbonyl (Cbz), 9-fluorenylmethyloxycarbonyl (FMOC), allyloxycarbonyl (Alloc), phthaloyl, benzoyl, and pivaloyl. Reference is made to T. W. Greene and P. G. M. Wuts, *Protective Groups in Organic Synthesis*, 2$^{nd}$ Edition (1991) for a description of other primary amine protecting groups which may be employed in the present process.

The second Sonogashira coupling partner is a 2,5-dihalopyridine. In one embodiment, the 2,5-dihalopyridine is 2,5-dibromopyridine. However, 2,5-dichloropyridine, 2,5-diiodopyridine, or a mixed 2,5-dihalopyridine, such as 2-chloro-5-bromo-pyridine, may also be employed in the reaction.

The double Sonogashira reaction of a 2,5-dihalopyridine is effected with the optionally protected propargylamine in the presence of a palladium catalyst and a base.

The Sonogashira reaction is optionally carried out in a suitable organic solvent, such as THF, benzene, toluene, dioxane, acetonitrile, aqueous acetonitrile, DME, DMSO, DMF, DMAC, and NMP, or a mixture of these solvents, such as THF/DMF.

Palladium catalysts which may be used in the Sonogashira reaction include a palladium alkanoate, a palladium acetonate, a palladium halide, a palladium halide complex, a palladium-dibenzylidene acetone complex, and a tri-arylphosphine palladium complex. More specifically, the palladium catalyst is selected from the group consisting of Pd(II) acetate, Pd(II) acetylacetonate, Pd(0)bis-dibenzylidene acetone ("dba"), Pd(II) bromide, Pd(II) chloride, Pd(II) iodide, Pd(II) sulfate, Pd(II) trifluoroacetate, $Pd(II)Cl_2(CH_3CN)_2$, $Pd_2(dba)_3$, $Pd(II)(dppf)Cl_2$, $Pd(II)Cl_2(PPh_3)_2$, $Pd(PPh_3)_4$, and $Pd(II)Cl_2(PhCN)_2$. In one embodiment the palladium catalyst is $Pd(II)Cl_2(PPh_3)_2$.

Bases which may be employed in the process of the present invention include organic aliphatic amines, such as triethylamine, diethylamine, diisopropylamine, diisopropylethylamine, n-butylamine, t-butylamine, 1,4-diazabicyclo[2.2.2]octane (DABCO), and quinuclidine, and organic aromatic amines, such as pyridine and 4-dimethylaminopyridine (DMAP). In one embodiment, the organic amine may serve as the reaction solvent as well as the base. In a class of this embodiment, the organic amine is diisopropylamine. Inorganic bases, such as potassium carbonate, may also be used in place of the organic amine.

The reaction is performed at a temperature range of about 10° C. to about 120° C. In another embodiment, the optionally protected propargylamine is used in an amount of about 2 to 3 molar equivalents of the 2,5-dihalopyridine.

In another embodiment of the process of the present invention, the Sonogashira reaction is carried out in the presence of a copper, zinc, or zirconium reagent. The addition of a copper, zinc, or zirconium reagent accelerates the rate of the coupling reaction. In one embodiment, the copper reagent is copper metal, a copper(I) halide, such as CuCl, CuBr, and CuI, or a copper(II) halide, such as $CuCl_2$, $CuBr_2$, and $CuI_2$. In a class of this embodiment, the copper reagent is CuBr or CuI. However, other copper(I) and copper(II) salts may also be utilized to accelerate the coupling reaction, such as copper(I) acetate and copper(I) cyanide. In another embodiment, the zinc reagent is zinc metal or a zinc salt, such as $ZnCl_2$, $ZnBr_2$, $ZnI_2$, or $Zn(OTf)_2$. In a further embodiment, the zirconium reagent is bis(cyclopentadienyl)zirconium dichloride.

The double Sonogashira reaction product is a compound of structural formula II:

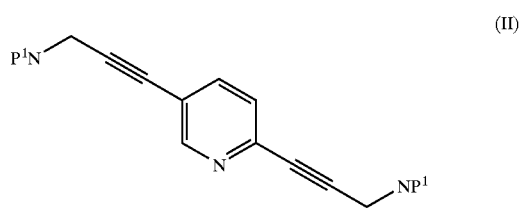

(II)

wherein $P^1$ is $H_2$ or a primary amine protecting group. The next step of the process is hydrogenation of the two triple bonds in structure II to afford a compound of structural formula IV. The hydrogenation is typically carried out in a solvent, such as THF, lower alkanol, such as methanol and ethanol, or aqueous lower alkanol, such as aqueous methanol and aqueous ethanol, at a hydrogen gas pressure of about 1 atmosphere to about 120 p.s.i., in the presence of a noble metal catalyst, such as Raney nickel, Pd/C, Rh/C, Ru/C, $Pd/Al_2O_3$, $PtO_2$, Pt/C, $Pt/Al_2O_3$, $Rh/Al_2O_3$, and $Ru/Al_2O_3$.

The last step of this aspect of the process of the present invention is the removal of the protecting groups $P^1$ in intermediate IV to generate the compound of structural formula I. When the primary amine protecting group is acetyl or formyl, it may be cleaved by treatment with aqueous acid or base preferably at an elevated temperature. In one embodiment, the acetyl or formyl group is cleaved by heating in aqueous hydrochloric acid. When the primary amine protecting group is t-butyloxycarbonyl, it may be cleaved by treatment with trifluoroacetic acid, sulfuric acid, HCl in ethyl acetate, HCl in diethyl ether, or HCl in dioxane. When the primary amine protecting group is benzyloxycarbonyl, reduction of the two triple bonds in structure II and removal of the $P^1$ protecting groups may be effected in one step, such as by catalytic hydrogenation. Other protecting groups can be removed by standard literature conditions, such as those found in T. W. Greene and P. G. M. Wuts, *Protective Groups in Organic Synthesis, 2nd* Edition (1991) and P. J. Kocienski, *Protecting Groups*, Georg Thieme Verlag, New York, 1994.

Another aspect of the present invention concerns a process of preparing a compound of structural formula I, wherein $P^1$ is a primary amine protecting group,

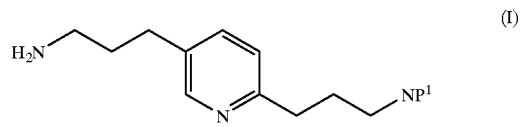

(I)

which comprises the steps of:

(a) producing a compound of structural formula V:

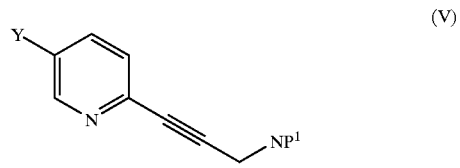

(V)

wherein Y is Cl, Br, or I; by reacting a 2,5-dihalopyridine with a protected propargylamine of structural formula III:

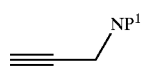
(III)

in the presence of a palladium catalyst and a base;
(b) producing a compound of structural formula VI:

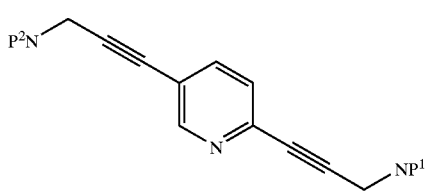
(VI)

wherein $P^1$ and $P^2$ are orthogonal primary amine protecting groups, by reacting a compound of structural formula V:

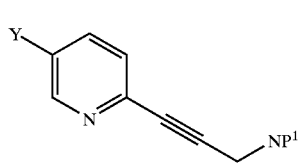
(V)

with a protected propargylamine of structural formula VII:

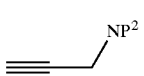
(VII)

in the presence of a palladium catalyst and a base;
(c) producing a compound of structural formula VIII:

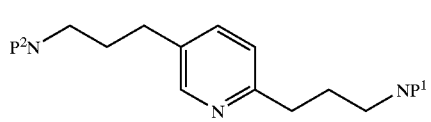
(VIII)

by hydrogenating a compound of structural formula VI:

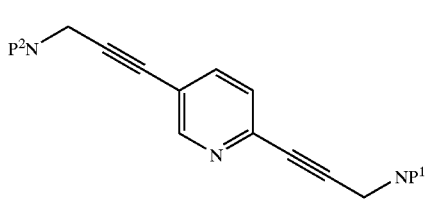
(VI)

and (d) selectively removing the primary amine protecting $P^2$ in a compound of structural formula VIII:

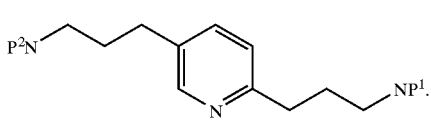
(VIII)

The key steps in this second aspect of the process of the present invention to prepare compounds of structural formula I involve two consecutive Sonogashira coupling reactions of a 2,5-dihalopyridine with two different orthogonally protected propargylamines of structural formulae III and VII. The first Sonogashira coupling reaction takes place at the more reactive C-2 position of the pyridine ring to afford a compound of structural formula V. The second Sonogashira coupling reaction takes place at the C-5 position of the pyridine ring to afford a compound of structural formula VI. The two consecutive Sonogashira coupling reactions may be performed in a single pot by first reacting the 2,5-dihalopyridine with a protected propargylamine of structural formula III in the presence of a palladium catalyst and a base and allowing the reaction to go to completion and subsequently adding a second protected propargylamine of structural formula VII and allowing the reaction to go to completion. Alternatively, the intermediate compound of structural formula V may be isolated after the first coupling reaction with III and then subjected to a second Sonogashira coupling reaction with a protected propargylamine of structural formula VII. The two triple bonds in the compound of structural formula VI are then reduced by hydrogenation to afford a compound of structural formula VIII. The final step in the process involves the selective removal of the protecting group $P^2$ in the compound of structural formula VIII without removing protecting group $P^1$ to afford a compound of structural formula I. Protecting groups $P^1$ and $P^2$ are chosen such that $P^2$ can be selectively cleaved under reaction conditions that do not affect $P^1$. An example of such an orthogonal pair of protecting groups is provided by $P^1$ as t-butyloxycarbonyl (t-Boc) and $P^2$ as benzyloxycarbonyl (Cbz) wherein the benzyl carbamate can be selectively cleaved under hydrogenolytic conditions without affecting the t-butyl carbamate group. These hydrogenolytic conditions will also reduce the triple bonds in a compound of formula VI such that the desired compound of formula I is obtained in a single step from intermediate VI.

The first coupling reaction with intermediate III is performed at a temperature range of about 10° C. to about 30° C. The $P^1$ protected propargylamine III is used in an amount of about 0.95 to about 1.2 molar equivalents of the 2,5-dihalopyridine. The second coupling reaction with intermediate VII is performed at a temperature range of about 10° C. to about 90° C. The $P^2$ protected propargylamine VII is used in an amount of about 0.95 to about 2.0 molar equivalents of the 2,5-dihalopyridine.

In one embodiment of this second aspect of the present invention, the Sonogashira coupling reaction is carried out in the presence of a copper reagent, such as copper(I) bromide and copper(I) iodide, or a zinc reagent, such as $ZnCl_2$ and $ZnBr_2$.

Compounds of structural formula I of the present invention can be converted into 3-(5,6,7,8-tetrahydro-[1,8]-naphthyridin-2-yl)-propylamine (IX) as described in GB 2,356,630 (May 30, 2001). Compound IX is a useful intermediate in the preparation of αv integrin receptor antagonists as described in WO 01/34602.

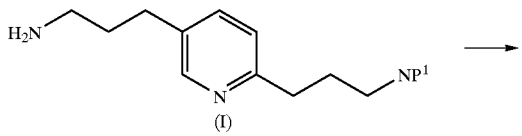
(I)

-continued

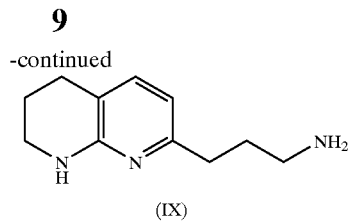

(IX)

Another aspect of the present invention is concerned with novel compounds which are useful intermediates in the preparation of the compounds of structural formula I. One embodiment of this aspect of the present invention comprises compounds of the structural formula:

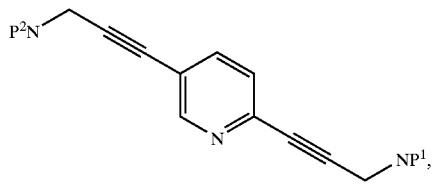

wherein $P^1$ and $P^2$ are each independently selected from the group consisting of hydrogen, acetyl, formyl, benzoyl, pivaloyl, phthaloyl, t-butyloxycarbonyl, benzyloxycarbonyl, allyloxycarbonyl, and 9-fluorenylmethyloxycarbonyl. In one embodiment of the novel compounds, both $P^1$ and $P^2$ represent acetyl, formyl, or benzyloxycarbonyl. In a second embodiment, $P^1$ is t-butyloxycarbonyl and $P^2$ is benzyloxycarbonyl.

A second embodiment of this aspect of the present invention comprises compounds of the structural formula:

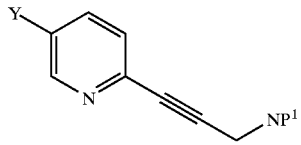

wherein Y is Cl, Br, or I and $P^1$ is selected from the group consisting of acetyl, formyl, benzoyl, pivaloyl, phthaloyl, t-butyloxycarbonyl, benzyloxycarbonyl, allyloxycarbonyl, and 9-fluorenylmethyloxycarbonyl.

Abbreviations: AcOH is acetic acid; BuLi is n-butyl lithium; $CH_2Cl_2$ is dichloromethane; DMAC is N,N-dimethylacetamide; DME is 1,2-dimethoxyethane; DMF is N,N-dimethylformamide; DMPU is 1,3-dimethyl-3,4,5,6-tetrahydro-2(1H)-pyrimidinone; DMSO is dimethyl sulfoxide; EtOAc is ethyl acetate; $Et_3N$ is triethylamine; $K_2CO_3$ is potassium carbonate; $MgSO_4$ is magnesium sulfate; MTBE is methyl t-butyl ether; NMR is nuclear magnetic resonance; $Na_2CO_3$ is sodium carbonate; $NaHCO_3$ is sodium hydrogencarbonate; and THF is tetrahydrofuran.

By halide is meant chloride, bromide, or iodide.

By lower alkanol is meant a $C_{1-5}$ linear or branched-chain alkyl alcohol, such as methanol, ethanol, isopropanol, and 1-butanol.

By "orthogonal protection" is meant two different protecting groups for each primary amino group on compounds of structural formulae VI and VIII, the removal of each of which is accomplished in any order with reagents and conditions which do not affect the other protecting group. An example of such orthogonal protection is benzyloxycarbonyl for one primary amino group and t-butyloxycarbonyl for the other primary amino group.

Representative experimental procedures utilizing the novel process of the present invention are detailed below. They are given for purposes of illustration only and are not intended to limit the process of the present invention to the specific conditions given for making the exemplified compounds.

Preparation of N-Protected Propargylamines:
N-Formylpropargylamine:
Step A: Sodium diformylamide

To a solution of sodium methoxide in methanol (25.4 wt %, 362 g) and formamide (168 g) was added 1,2-dimethoxyethane (200 mL). The mixture was distilled and additional 1,2-dimethoxyethane (850 mL) was added at a rate such that by the end of the addition (3.5 h) a total of 1200 mL of distillate had been collected. The mixture was cooled to 20–25° C. and filtered. The cake was dried to afford 158 g of sodium diformylamide.

$^1$H NMR (DMSO-$d_6$; 400 MHz): δ 8.96 (s).
$^{13}$C NMR (DMSO-$d_6$; 101 MHz): δ 180.6.

Step B: N-formylpropargylamine

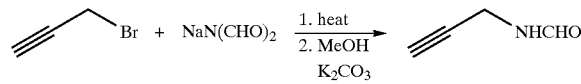

To a slurry of sodium diformylamide (157 g) in acetonitrile (1 L) was added propargyl bromide (80 wt % in toluene, 149 mL), and the mixture was heated to reflux for 11 h. The mixture was cooled to 20–25° C, methanol (123 mL) and potassium carbonate (49 g) were added, and the mixture was stirred at ambient temperature for 1 h. The mixture was filtered, and the filtrate was concentrated at reduced pressure to give an oil. The oil was redissolved in methylene dichloride (200 mL), the solution was filtered through a pad of silica gel (100 g), and the filtrate was concentrated at reduced pressure to afford crystalline N-formylpropargylamine (112 g).

$^1$H NMR (CDCl$_3$; 400 MHz): major rotamer δ 8.13 (s, 1H), 6.94 (br, 1H), 4.02 (ddd, J=5.6, 2.6, 0.8 Hz, 2H), 2.23 (t, J=2.6 Hz, 1H); minor rotamer δ 8.09 (d, J=12.1 Hz, 1 H), 6.51 (br, 1 H), 3.97 (dd, J=6.0 and 2.6 Hz, 2 H), 2.34 (t, J=2.6 Hz, 1 H).

$^{13}$C NMR (CDCl$_3$; 101 MHz): major rotamer δ 161.4, 78.9, 71.3, and 27.4; minor rotamer δ 164.7, 78.7, 72.8, and 31.2.

N-Acetylpropargylamine:

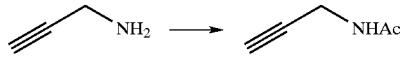

To a solution of propargylamine (20.0 g) and triethylamine (69.7 mL) in ethyl acetate (500 mL) was slowly added acetyl chloride (33.6 mL), maintaining the inner temperature below 30° C. The mixture was aged at ambient temperature overnight. Water (130 mL) was added to the mixture. The resulting organic layer was separated. The aqueous layer was extracted with ethyl acetate (100 mL) then dichloromethane (100 mL×6) after saturating the aqueous layer with sodium chloride. The organic layers were combined, dried over magnesium sulfate, and concentrated under reduced pressure. The residue was crystallized from ethyl acetate (50 mL). The crystals were collected by filtration, washed with ethyl acetate, and dried to give 22.1 g of the title compound. The filtrate and wash were combined and purified by silica gel column chromatography with ethyl acetate as eluant. The fractions containing the title compound were combined, concentrated, and crystallized from MTBE to give an additional 9.33 g of the title compound.

¹H NMR (CDCl₃; 400 MHz): δ 6.09 (broad s, 1H), 4.03 (dd, J=5.2 and 2.8 Hz, 2H), 2.22 (t, J=2.8 Hz, 1H), and 2.01 (s, 3H).

¹³C NMR (CDCl₃; 101 MHz): δ 169.9, 79.5, 71.4, 29.2, and 22.9.

N-Cbz-propargylamine:

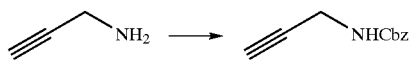

To a solution of propargylamine (20 g) and triethylamine (60.7 mL) in ethyl acetate (500 mL) was added benzyloxycarbonyl chloride (71.7 g) slowly while maintaining the reaction temperature between −5° C. and +5° C. The mixture was then stirred at room temperature overnight. The mixture was washed sequentially with 1.5 M HCl (200 mL), 5% NaHCO₃ in water (200 mL), and saturated aqueous sodium chloride (100 mL). The solvent was switched to hexane while the desired product precipitated as colorless crystals (60.1 g).

¹H NMR (CDCl₃; 400 MHz): δ 7.40–7.30 (m, 5H), 5.14 (s, 2H), 5.01 (broad s, 1H), 4.00 (m, 2H), and 2.25 (t, J=2.4 Hz, 1H).

¹³C NMR (CDCl₃; 101 MHz): δ 155.9, 136.2, 128.5, 128.22, 128.17, 79.6, 71.6, 67.1 and 30.9.

N-Boc-propargylamine:

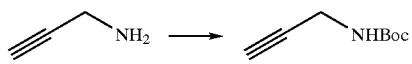

To di-tert-butyl dicarbonate (25.3 mL) was added propargylamine (7.11 mL) under ice-cooling. The mixture was aged at ambient temperature overnight. The mixture was concentrated under reduced pressure, and the residue was diluted with hexane and further concentrated under reduced pressure. The resulting crystalline residue was triturated with hexanes, collected by filtration, and dried to give 12.5 g of the title compound.

¹H NMR (CDCl₃; 400 MHz): δ 4.79 (broad s, 1H), 3.91 (broad s, 2H), 2.21 (t, J=2.6 Hz, 1H), and 1.44 (s, 9H).

¹³C NMR (CDCl₃; 101 MHz): δ 155.2, 80.1, 80.0, 71.2, 30.3, and 28.3.

EXAMPLES OF SONOGASHIRA COUPLING REACTION

Example 1

N-[3-(5-Bromopyridin-2-yl)prop-2-ynyl]acetamide (1-2)

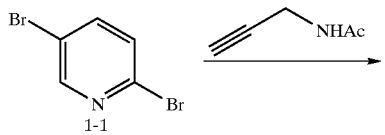

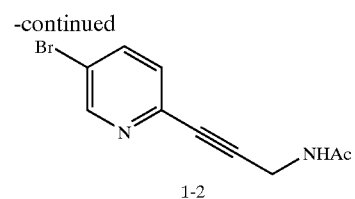

A mixture of 2,5-dibromopyridine (1-1) (1.19 g), N-acetyl-propargylamine (733 mg), CuI (10 mg), and Pd(PPh₃)₂Cl₂ (73 mg) in diisopropylamine (20 mL) was stirred at ambient temperature under nitrogen atmosphere over 3 days. The mixture was diluted with ethyl acetate (50 mL). The solid was filtered and washed with ethyl acetate. The filtrate and wash were combined and concentrated under reduced pressure. The residue was purified by silica gel column chromatography using ethyl acetate as eluant to give crystalline 1-2 (1.14 g).

¹H NMR (CD₃OD; 400 MHz): δ 8.67 (dd, J=2.4 and 0.8 Hz, 1H), 8.41 (broad t, J=5.6 Hz, 1H), 8.05 (dd, J=8.4 and 2.4 Hz, 1H), 8.43 (dd, J=8.4 and 0.8 Hz, 1H), 4.11 (d, J=5.6 Hz, 2H), 1.85 (s, 3H).

¹³ NMR (CD₃OD, 101 MHz): δ 169.5, 151.3, 141.3, 139.9, 128.9, 120.4, 88.8, 80.8, 28.8, and 22.8.

Example 2

N-(3-{5-[3-(acetamido)prop-1-ynyl]pyridin-2-yl}prop-2-ynyl)acetamide (2-1)

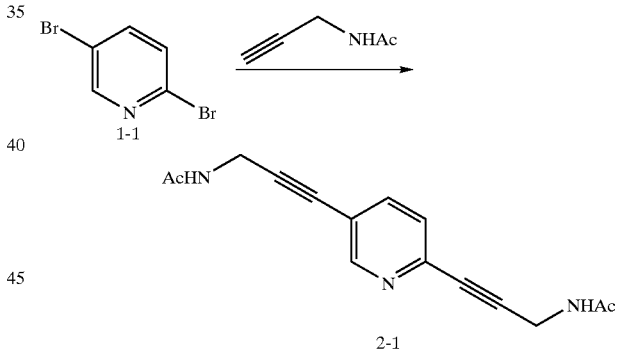

A mixture of 2,5-dibromopyridine (15.0 g, 63.9 mmol), N-acetyl-propargylamine (15.51 g), and PdCl₂(PPh₃)₂ (453 mg) in diisopropylamine (510 mL) was refluxed for 3 hours under a nitrogen atmosphere. To the mixture was added water (200 ml) and diisopropylamine was removed from the mixture by distillation under reduced pressure. The resulting suspension was aged at ambient temperature for 1 hour, and precipitates were collected by filtration and dried under reduced pressure to provide 2-1 (14.0 g).

¹H NMR (CD₃OD; 400 MHz): δ 8.55 (dd, J=2.4 and 0.8 Hz, 1H), 8.44–8.36 (m, 2H), 7.82 (dd, J=8.0 and 2.4 Hz, 1H), 7.47 (dd, J=8.0 and 0.8 Hz, 1H), 4.131 (d, J=5.6 Hz, 2H), 4.127 (d, J=5.6 Hz, 2H), 1.85 (s, 3H), and 1.84 (s, 3H).

¹³C NMR (CD₃OD; 101 MHz): δ 171.54, 171.51, 151.5, 141.1, 139.3, 126.6, 119.6, 90.6, 87.8, 80.5, 78.0, 28.8, 28.6, 20.95, and 20.94.

Example 3 tert-Butyl 3-(5-bromopyridin-2-yl)prop-2-ynylcarbamate (3-1)

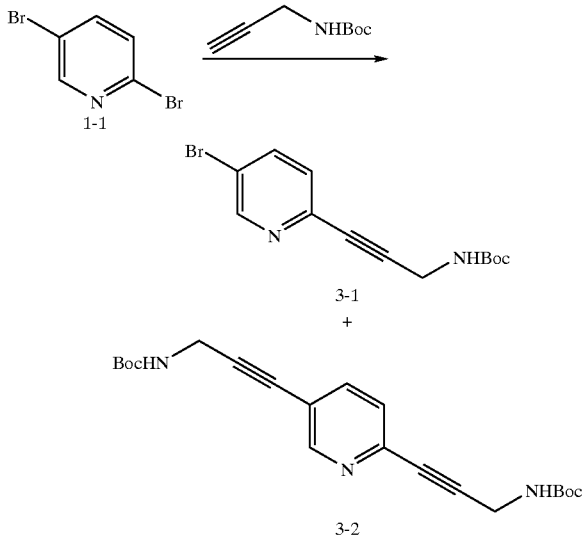

A mixture of 2,5-dibromopyridine (1.19 g), N-Boc-propargylamine (790 mg), Pd(PPh$_3$)$_2$Cl$_2$ (73 mg), and CuI (10 mg) in diisopropylamine (20 mL) was stirred at ambient temperature under nitrogen atmosphere overnight. The mixture was diluted with ethyl acetate (70 mL) and the precipitates were filtered off and washed with ethyl acetate. The filtrate and washings were combined, concentrated under reduced pressure, and purified by silica gel column chromatography using a mixture of hexanes and MTBE (3:2 to 2:3). The fractions containing the title compound were combined and concentrated under reduced pressure to give crystalline 3-1 (1.58 g, containing 1.9 wt 5 MTBE). The fractions containing a more polar compound were combined and concentrated under reduced pressure to give tert-butyl 3-(5-{3-{(tert-butoxycarbonyl)amino]prop-1-ynyl}pyridin-2-yl}prop-2-ynylcarbamate (3-2) (50 mg).

tert-butyl 3-(5-bromopyridin-2-yl)prop-2-ynylcarbamate (3-1)

$^1$H NMR (CDCl$_3$; 400 MHz): δ 8.62 (d, J=2.4 Hz, 1H), 7.78 (dd, J=8.4 and 2.4 H 1H), 7.30 (d, J=8.4Hz, 1H), 4.83 (broad s, 1H), 4.18 (d, J=5.2Hz, 2H), and 1.47 (s, 9H).
$^{13}$C NMR (CDCl$_3$; 101 MHz): δ 155.2, 151.1, 141.2, 138.9, 128.0, 120.2, 87.1, 81.5, 80.1, 31.0, and 28.3.

tert-butyl 3-(5-{3-{(tert-butoxycarbonyl)amino]prop-1-ynyl}pyridin-2-yl}prop-2-ynylcarbamate (3-2)

$^1$H NMR (CDCl$_3$; 400 MHz): δ 8.55 (d, J=2.0 Hz, 1H), 7.61 (dd, J=8.0 and 2.0 Hz, 1H), 7.31 (d, J=8.0 Hz, 1H), 4.96 (broad s, 2H), 4.24–4.05 (m. 4H), 1.45 (s, 9H), and 1.44 (s, 9H).
$^{13}$C NMR (CDCl$_3$; 101 MHz): δ 155.3, 152.4, 141.5, 138.7, 126.2, 119.1, 90.8, 87.6, 82.1, 80.1, 79.4, 31.0, and 28.3.

Example 4

2-[3-(5-Bromopyridin-2-yl)prop-2-ynyl]-1H-isoindole-1,3(2H)-dione (4-1)

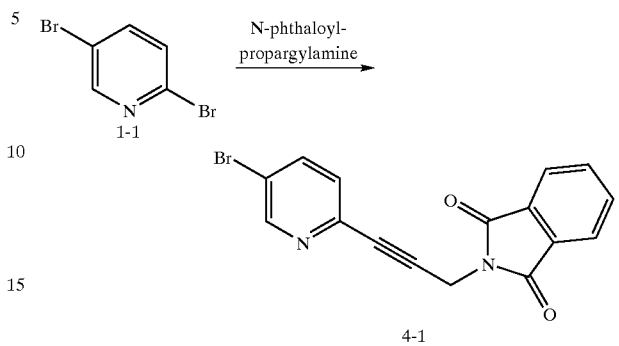

A mixture of 2,5-dibromopyridine (2.38 g), N-phthaloyl-propargylamine (2.78 g), Pd(PPh$_3$)$_2$Cl$_2$ (146 mg), and CuI (20 mg) in diisopropylamine (20 mL) was stirred at ambient temperature overnight under nitrogen atmosphere. The mixture was diluted with acetone. The precipitates were filtered, washed with water, and dried under reduced pressure to give 4-1 (3.28 g) as a solid.
$^1$H NMR (DMSO-d$_6$; 400 MHz): δ 8.63 (broad s, 1H), 8.02 (broad d, J=8.0 Hz, 1H), 7.95–7.83 (m, 4H), 7.46 (d, J=8.0 Hz, 1H), and 4.65 (s, 2H).
$^{13}$C NMR (DMSO-d$_6$; 101 MHz): δ 167.2, 151.3, 140.7, 139.9, 135.2, 131.9, 129.2, 123.9, 120.8, 85.4, 81.4, and 27.8.

Example 5

2-(3-{5-[3-(1,3-Dioxo-1,3-dihydro-2H-isoindol-2-yl)prop-1-ynyl]pyridin-2-yl}prop-2-ynyl)-1H-isoindole-1,3(2H)-dione (5-1)

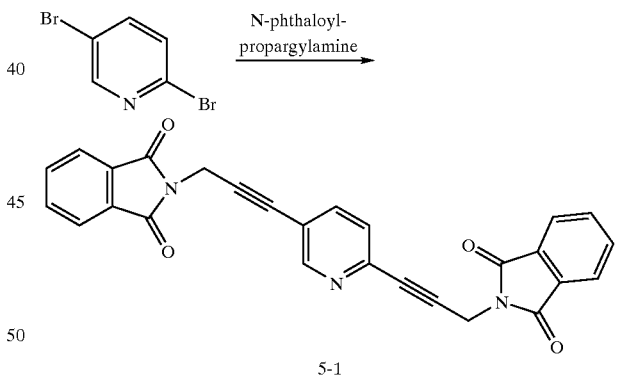

A mixture of 2,5-dibromopyridine (1.19 g), N-phthaloyl-propargylamine (2.33 g), Pd(PPh$_3$)$_2$Cl$_2$ (73 mg), and CuI (10 mg) in diisopropylamine (60 mL) was heated under reflux under a nitrogen atmosphere overnight. The precipitates were collected by filtration, washed with diethyl ether then water, and dried to give crude 5-1 (2.51 g). The compound was further purified by silica gel column chromatography using ethyl acetate as eluant.
$^1$H NMR (DMSO-d$_6$; 400 MHz): δ 8.55 (d, J=2.0 Hz, 1H), 7.95–7.84 (m, 8 H), 7.83 (dd, J=8.0 and 2.0 Hz, 1H), 7.48 (d, J=8.0 Hz, 1H), and 4.67 (s, 4H).
$^{13}$C NMR (DMSO-d$_6$; 101 MHz): δ167.2, 152.6, 141.2, 139.7, 135.20, 135.17, 131.94, 131.91, 127.3, 123.8, 118.8, 89.6, 86.1, 81.8, 79.2, 27.9 and 27.8.

Example 6

Benzyl 3-(6-{3-[(tert-butoxycarbonyl)amino]prop-1-ynyl}pyridin-3-yl)prop-2-ynylcarbamate (6-1)

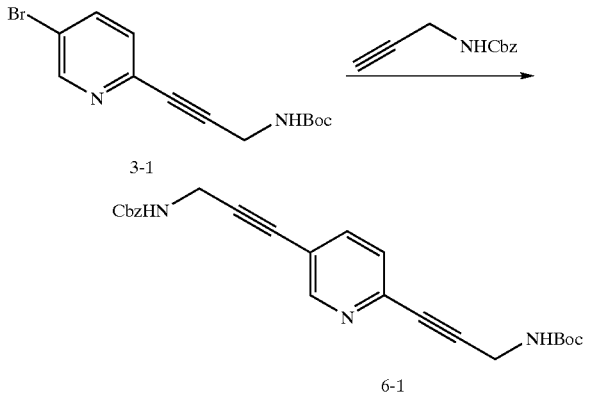

A mixture of tert-butyl 3-(5-bromopyridin-2-yl)prop-2-ynylcarbamate (3-1) (1.44 g), N-Cbz propargylamine (1.09 g), Pd(PPh₃)₂Cl₂ (73 mg), and CuI (10 mg) in diisopropylamine (25 mL) was heated under reflux under a nitrogen atmosphere for 3 hours. The mixture was cooled to ambient temperature and diluted with ethyl acetate (70 mL). The precipitates were filtered and rinsed with ethyl acetate (30 mL). The filtrate and washings were combined, concentrated under reduced pressure, and purified by silica gel column chromatography using a mixture of MTBE and hexanes (2:3 to 4:1). The fractions containing the product were combined and concentrated under reduced pressure. The residue was crystallized from MTBE. Crystals were filtered, washed with MTBE, and dried to give 6-1 (1.07 g). An additional 120 mg of 6-1 was isolated from the mother liquors and washings.

¹H NMR (CDCl₃: 400 MHz): δ 8.56 (s, 1H), 7.62 (d, J=7.6 Hz, 1H), 7.41–7.28 (m, 6 H), 5.25 (broad s, 1H), 5.15 (s, 2H), 4.92 (broad s, 1H), 4.24 (d, J=5.2 Hz, 2H), 4.18 (d, J=4.8 Hz, 2H), and 1.46 (s, 9H).
¹³C NMR (CDCl₃; 101 MHz): δ 155.9, 155.3, 152.4, 141.6, 138.7, 136.2, 128.5, 128.24, 128.17, 126.2, 119.0, 90.3, 87.7, 82.1, 80.1, 79.8, 67.2, 31.6, 31.0, and 28.3.

The title compound can also be prepared in a one-pot sequence from 2,5-dibromopyridine as described in Example 9.

Example 7

Benzyl 3-(5-bromopyridin-2-yl)prop-2-ynylcarbamate (7-1)

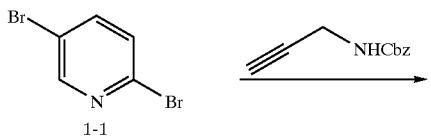

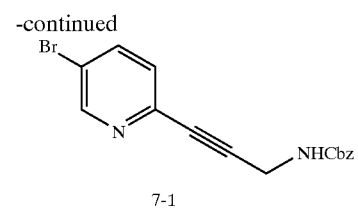

A mixture of 2,5-dibromopyridine (1.19 g), N-Cbz-propargylamine (1.04 g), Pd(PPh₃)₂Cl₂ (73 mg), and CuI (10 mg) in diisopropylamine (20 mL) was stirred at ambient temperature for 3 hours under nitrogen. The mixture was diluted with ethyl acetate (50 mL). The mixture was filtered and washed with ethyl acetate (20 mL). The filtrate and wash were combined, concentrated under reduced pressure and triturated in MTBE to give crystalline 7-1 (1.28 g). The mother liquor was further purified by silica gel column chromatography using a mixture of MTBE: hexanes (1:1) to give an additional 280 mg of 7-1.

¹H NMR (400 MHz; CDCl₃): δ 8.62 (d, J=2.3 Hz, 1H), 7.77 (dd, J=8.4, 2.3 Hz, 1H), 7.28–7.38 (m, 6H), 5.15 (m, 3H), and 4.25 (d, J=5.2 Hz, 2H).
¹³C NMR (101 MH; CDCl₃): δ 156.1, 151.4, 141.3, 139.1, 136.4, 128.8, 128.42, 128.35, 128.2, 120.6, 86.8, 82.1, 67.4, and 31.7.

Example 8

Benzyl 3-[5-(3-{[(benzyloxy)carbonyl]amino}prop-1-ynyl)pyridin-2-yl]prop-2-ynylcarbamate (8-1)

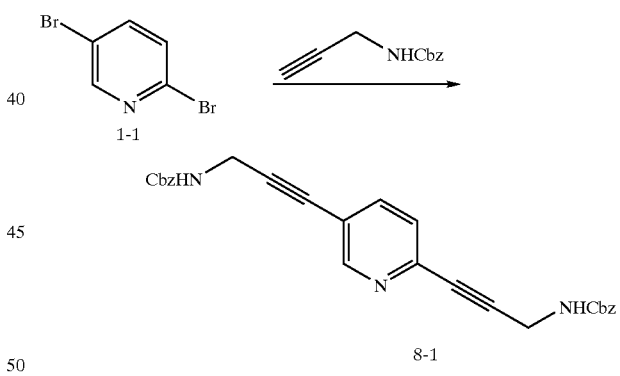

A mixture of 2,5-dibromopyridine (3.00 g), N-Cbz-propargylamine (5.99 g), PdCl₂(PPh₃)₂ (89.8 mg), and CuI (6.0 mg) in diisopropylamine (51 ml) was heated at 65° C. for 7 hours under nitrogen atmosphere. The mixture was cooled to room temperature, and the precipitates were filtered, washed with water, and dried under reduced pressure to give 8-1 (4.96 g) as a crystalline compound; m.p. 156–158° C.

¹H NMR (400 Hz; CDCl₃): δ 8.65 (broad s, 1H), 7.63 (d, J=7.6 Hz, 1H), 7.32-7.37 (m, 11H), 5.16 (s, 2H), 5.15 (s, 2H), 5.09 (broad s, 2H), and 4.24-4.28 (m, 4H).
¹³C NMR (101 MHz; CDCl₃): δ 156.1, 152.7, 141.7, 138.9, 136.40, 136.37, 128.69, 128.67, 128.5, 128.4, 126.5, 119.3, 90.5, 87.3, 82.6, 80.0, 67.32, 67.28, 31.8, and 31.7.

Example 9

Benzyl 3-(6-{3-[(tert-butoxycarbonyl)amino]prop-1-ynyl}pyridin-3-yl)prop-2-ynylcarbamate (6-1)

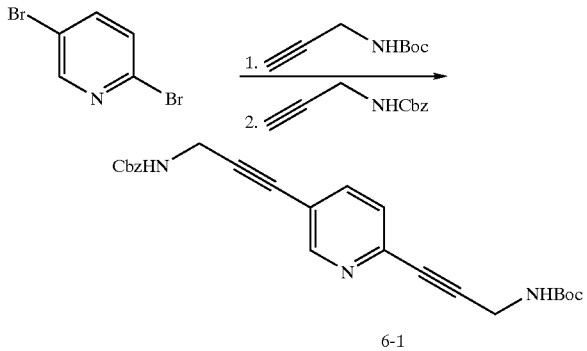

A mixture of 2,5-dibromopyridine (1.19 g), N-Boc-propargylamine (781 mg), Pd(PPh₃)₂Cl₂ (73 mg), and CuI (10 mg) in diisopropylamine (20 mL) was stirred at room temperature overnight under nitrogen atmosphere. To the mixture was added N-Cbz-propargylamine (1.14 g) and the mixture was heated under reflux temperature for 5 hours under nitrogen atmosphere. The mixture was cooled to room temperature. To the mixture was added ethyl acetate (50 mL). The precipitates were filtered and washed with ethyl acetate. The filtrate and washings were combined and purified by silica gel column to give 6-1 (250 mg) as a crystalline compound.

Example 10

N-(3-{5-[3-(Formamido)prop-1-ynyl]pyridin-2-yl}prop-2-ynyl)formamide (9-1)

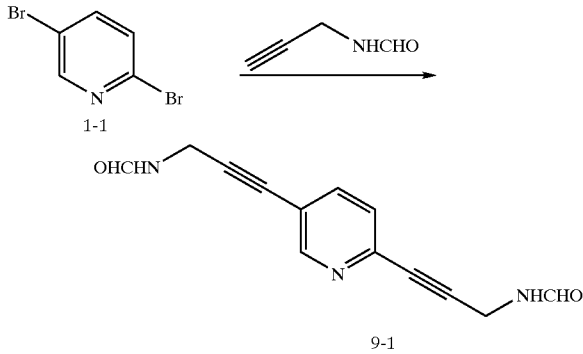

A mixture of 2,5-dibromopyridine (100 g), N-formylpropargylamine (87.7 g), PdCl₂(PPh₃)₂ (2.96 g), and CuI (0.2 g) in diisopropylamine (3 L) was heated at 70° C. for 6 h under a nitrogen atmosphere. The mixture was cooled to 20–22° C. and filtered. The cake was dried and then slurried in water (3 L) at 0–5° C. for 3 h. The slurry was filtered, and the cake was dried to afford 95.4 g of the title compound 9-1.

$^1$H NMR (DMSO-d₆; 400 MHz): δ 8.58 (br, 2H), 8.56 (d, J=2.0 Hz, 1H), 8.09 (s, 2H), 4.20 (d, J=5.6 Hz, 4H).

$^{13}$C NMR (DMSO-d₆; 101 MHz): δ 161.0, 152.0, 141.0, 139.0, 126.6, 118.6, 91.8, 88.3, 81.1, 78.3, 27.3, and 27.1.

EXAMPLES OF REDUCTION STEP

Example 11

N-(3-{5-[3-(Acetylamino)propyl]pyridin-2-yl}propyl)acetamide (10-1)

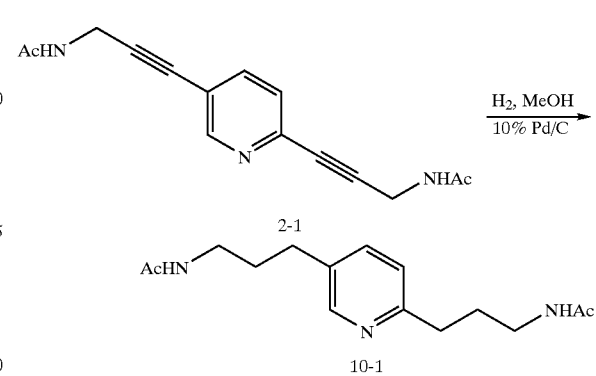

A mixture of N-(3-{5-[3-(acetamido)prop-1-ynyl]pyridin-2-yl}prop-2-ynyl)acetamide (2-1) (10 g), 10% Pd/C (1.5 g) in methanol (200 mL) was hydrogenated under 20 psi hydrogen at room temperature for 16 hours. The catalyst was removed by filtration using Solka-floc and washed with methanol. The filtrate and washings were combined and concentrated under reduced pressure to provide 10-1 as a crystalline compound (10.1 g); m.p. 95.2–97.8° C.

$^1$H NMR (400 MHz; CDCl₃): δ 8.18 (d, J=1.8 Hz, 1H), 7.31 (dd, J=1.8, 7.6 Hz, 1H), 7.08 (broad, 1H), 6.99 (broad, 1H), 6.96 (d, J=7.6 Hz, 1H), 3.15–3.09 (m, 4H), 2.66 (t, J=7.3 Hz, 2H), 2.48 (t, J=7.5 Hz, 2H), 1.84 (s, 3H), 1.83 (s, 3H) 1.79 (m, 2H), and 1.69 (m, 2H).

$^{13}$C NMR (101 MHz; CDCl₃): δ 170.6, 170.5, 158.6, 148.7, 136.6, 134.3, 122.6, 39.1, 38.9, 34.9, 30.7, 29.8, 29.0, 23.1, and 23.0.

Example 12

2-(3-{5-[3-(1,3-Dioxo-1,3-dihydro-2H-isoindol-2-yl)propyl]pyridin-2-yl}propyl)-1H-isoindole-1,3(2H)-dione (11-1)

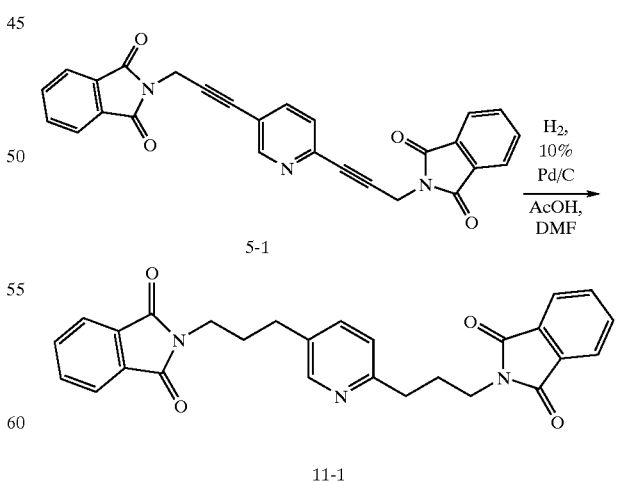

A mixture of 2-(3-{5-[3-(1,3-dioxo-1,3-dihydro-2H-isoindol-2-yl-prop-1-ynyl]pyridin-2-yl}prop-2-ynyl)-1H-isoindole-1,3(2H)-dione (5-1) (200 mg), 10% Pd/C (50 wt %; 60 mg), and acetic acid (1 mL) in DMF (1 mL) was stirred at ambient temperature under 1 atmosphere pressure of hydrogen for 2 days. The catalyst was removed by filtration through Solka-floc and washed with ethanol. The filtrate and wash were combined and concentrated under reduced pressure to give 11-1 (130 mg) as colorless crystals.

$^1$H NMR (400 MHz, CDCl$_3$): δ 8.31 (d, J=2.0 Hz, 1H), 7.85–7.80 (m, 4H), 7.72–7.68 (m, 4H), 7.42 (dd, J=8.0 and 2.0 Hz, 1H), 7.08 (d, J=8.0 Hz, 1H), 3.76 (t, J=7.2 Hz, 2H), 3.74 (t, J=7.2 Hz, 2H), 2.79 (t, J=7.6 Hz, 2H), 2.62 (t, J=7.8 Hz, 2H), 2.11 (m, 2H), and 1.98 (m, 2H).

$^{13}$C NMR (101 MHz, CDCl$_3$): δ 168.3, 158.4, 149.0, 136.2, 133.9, 133.8, 133.6, 132.1, 132.0, 123.2, 123.1, 122.4, 37.7, 37.6, 35.0, 29.9, 29.6, and 28.3.

Example 13

3-[5-(3-aminopropyl)pyridin-2-yl]propyl amine (12-1)

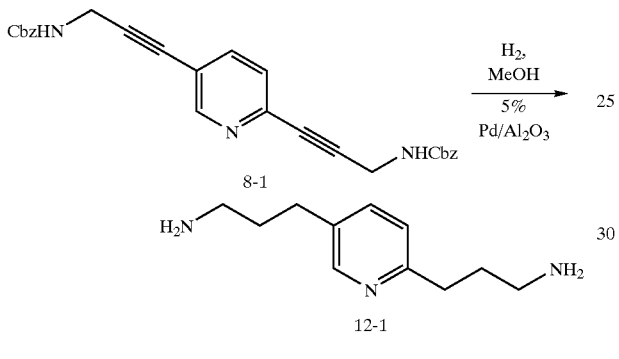

A solution of 2,5-di(3-benzyloxycarbonylaminoprop-1-ynyl)pyridine (8-1) (8.0 g) in methanol (160 mL) was hydrogenated under 20 psi of hydrogen gas pressure in the presence of 5%-Pd/Al$_2$O$_3$ (1.1 g) for 16 hours. The catalyst was filtered through Solka-flok and washed with methanol. The filtrate and wash were combined and concentrated under reduced pressure to give 12-1 (3.56 g) as a crystalline compound; m.p. 116–119° C.

$^1$H NMR (400 MHz; D$_2$O): δ 7.99 (d, J=2.0 Hz, 1H), 7.29 (dd, J=8.0, 2.0 Hz, 1H), 6.92 (d, J=8.0 Hs, 1H), 2.48 (t, J=7.7 Hz, 2H), 2.43–2.34 (m, 4H), 2.29 (t, J=7.7 Hz, 2H), 1.54 (pentet, J=7.7 Hz, 2H), and 1.42 (pentet, J=7.7 Hz, 2H).

$^{13}$C NMR (101 MHz; D$_2$O): δ 158.7, 147.8, 137.6, 135.5, 123.0, 40.4, 40.2, 34.1, 33.5, 32.6, and 29.2.

Example 14

N-(3-{5-[3-(Formylamino)propyl]pyridin-2-yl}propyl)formamide (13-1)

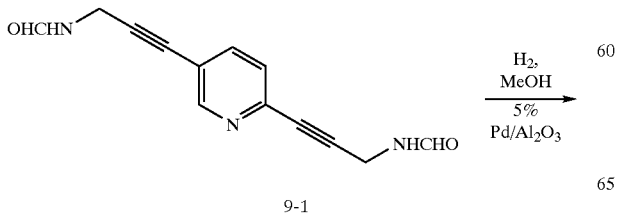

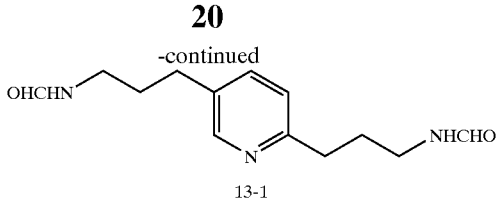

A mixture of N-(3-{5-[3-(formamido)prop-1-ynyl]pyridin-2-yl}prop-2-ynyl)formamide (9-1) (28 g) and 5% Pd/Al$_2$O$_3$ (2.8 g) in methanol (350 mL) was hydrogenated at 40 psi at ambient temperature for 5 h. The mixture was filtered through Solka Floc. The filtrate was concentrated to afford 13-1 as an oil.

$^1$H NMR (DMSO-d$_6$; 400 MHz): δ 8.32 (d, J=2.0 Hz, 1H), 8.04 (br, 2H), 8.01 (d, J=4.4 Hz, 2H), 7.53 (dd, J=8.0 and 2.0 Hz, 1H), 7.17 (d, J=8.0 Hz, 1H), 3.09 (quintet, J=6.8 Hz, 4H), 2.69 (t, J=7.6 Hz, 2H), 2.56 (t, J=7.6 Hz, 2H), 1.78 (t, J=7.2 Hz, 2H), and 1.69 (t, J=7.6 Hz, 2H).

$^{13}$C NMR (DMSO-d$_6$; 101 MHz): δ 161.1, 161.0, 158.4, 148.8, 136.4, 134.2, 122.4, 48.6, 36.9, 36.6, 34.3, 30.5, and 29.1.

EXAMPLES OF REMOVAL OF N-DEPROTECTION

Example 15

Preparation of 3-[5-(3-aminopropyl)pyridin-2-yl]propylamine (12-1)

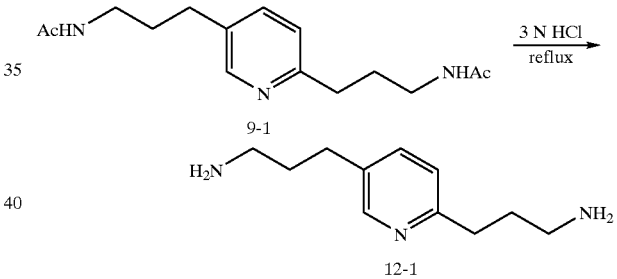

A solution of N-(3-{5-[3-(acetylamino)propyl]pyridin-2-yl}propyl)acetamide (9-1) (1.5 g) in 3N HCl (15 mL) was heated under reflux for 3 hours. At room temperature, 5N NaOH (about 10 mL) was added to the solution until a pH of about 10 was achieved. The solution was extracted three times with sec-butyl alcohol (15 mL). The extracts were combined and concentrated under reduced pressure to give 12-1 (2 g). The melting point and NMR spectra were identical to those observed for 12-1 in Example 13.

Example 16

3-[5-(3-Aminopropyl)pyridin-2-yl]propylamine (12-1)

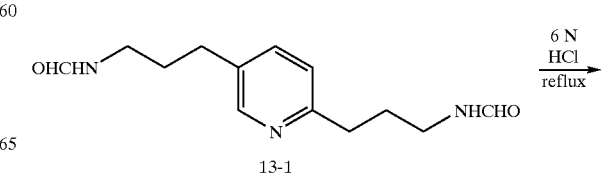

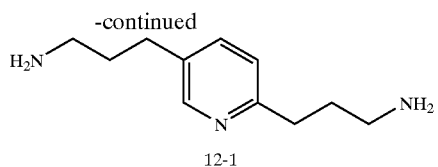

12-1

A solution of N-(3-{5-[3-(formylamino)propyl]pyridin-2-yl}propyl)formamide (13-1) (13.25 g) in 6N HCl (100 mL) was refluxed for 1.5 h. The solution was cooled to 0–5° C. and the pH was adjusted to pH 12.5 with 50% sodium hydroxide (35 mL). The solution was extracted three times with s-BuOH, the extracts were combined, and the solvent was switched to toluene. The solution contained 10.0 g of the title compound 12-1 as determined by HPLC assay.

What is claimed is:

1. A process for preparing the compound of structural formula Ia:

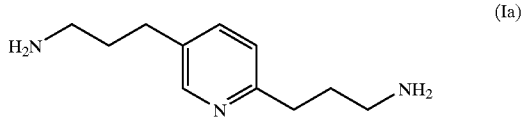

(Ia)

which comprises the steps of:
(a) hydrogenating a compound of structural formula II:

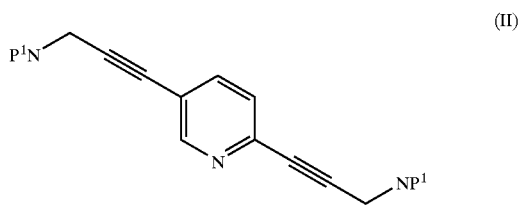

(II)

wherein $P^1$ is $H_2$ or a primary amine protecting group; and
(b) removing the primary amine protecting groups $P^1$, when $P^1$ represents a primary amine protecting group, wherein the compound of structural formula II is produced by reacting a 2,5-dihalopyridine with an optionally protected propargylamine of structural formula III:

(III)

in the presence of a palladium catalyst and a base.

2. The process of claim 1 wherein the palladium catalyst is selected from the group consisting of a palladium alkanoate, a palladium acetonate, a palladium halide, a palladium halide complex, a palladium-dibenzylidene acetone complex, and a triarylphosphine palladium complex.

3. The process of claim 2 wherein the palladium catalyst is selected from the group consisting of Pd(II) acetate, Pd(II) acetylacetonate, Pd(0)bis-dibenzylidene acetone ("dba"), Pd(II) bromide, Pd(II) chloride, Pd(II) iodide, Pd(II) sulfate, Pd(II) trifluoroacetate, $Pd(II)Cl_2(CH_3CN)_2$, $Pd_2(dba)_3$, $Pd(II)(dppf)Cl_2$, $Pd(II)Cl_2(PPh_3)_2$, $Pd(PPh_3)_4$, and $Pd(II)Cl_2(PhCN)_2$.

4. The process of claim 3 wherein the palladium catalyst is $Pd(II)Cl_2(PPh_3)_2$.

5. The process of claim 1 wherein the reaction is carried out in an organic solvent is selected from the group consisting of acetonitrile, aqueous acetonitrile, THF, benzene, toluene, dioxane, DME, DMSO, DMF, DMAC, NMP, and mixtures thereof.

6. The process of claim 1 wherein the base is selected from the group consisting triethylamine, diethylamine, diisopropylamine, diisopropylethylamine, n-butylamine, t-butylamine, 1,4-diazabicyclo[2.2.2]octane, quinuclidine, pyridine, and 4-dimethylaminopyridine.

7. The process of claim 6 wherein the base is diisopropylamine.

8. The process of claim 1 wherein the 2,5-dihalopyridine is 2,5-dibromopyridine.

9. The process of claim 1 wherein the reaction is carried out at a temperature of about 0° C. to about 100° C.

10. The process of claim 1 wherein the primary amine protecting group $P^1$ is selected from the group consisting of phthaloyl, benzyloxycarbonyl, t-butyloxycarbonyl, allyloxycarbonyl, 9-fluorenylmethyloxycarbonyl, acetyl, formyl, benzoyl, and pivaloyl.

11. The process of claim 10 wherein the primary amine protecting group $P^1$ is acetyl or formyl.

12. The process of claim 10 wherein the primary amine protecting group $P^1$ is benzyloxycarbonyl.

13. The process of claim 12 wherein steps (a) and (b) are carried out in a single step by hydrogenation.

14. The process of claim 1 wherein the propargylamine is used in an amount of about 2 to about 3 molar equivalents of said 2,5-dihalopyridine.

15. The process of claim 1 wherein the reaction is carried out in the presence of a copper, zinc, or zirconium reagent.

16. The process of claim 15 wherein the copper reagent is selected from the group consisting of copper metal, copper (I) chloride, copper(I) bromide, copper(I) iodide, copper(II) chloride, copper(II) bromide, and copper(II) iodide.

17. The process of claim 16 wherein the copper reagent is copper(I) bromide or copper(I) iodide.

* * * * *